(12) United States Patent
State et al.

(45) Date of Patent: Dec. 9, 2008

(10) Patent No.: US 7,461,741 B2

(54) PACKAGING FOR MEDICAL DEVICE

(75) Inventors: Matt State, Rosemount, MN (US);
Jeremy Kister, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 11/148,591

(22) Filed: Jun. 9, 2005

(65) Prior Publication Data
US 2006/0278546 A1  Dec. 14, 2006

(51) Int. Cl.
*B65D 83/10* (2006.01)

(52) U.S. Cl. .................. 206/364; 206/438; 600/585

(58) Field of Classification Search .......... 206/53, 206/54, 225, 227, 303, 363, 364, 388, 438; 220/23.4, 23.8; 242/159, 172; 600/585; 604/159, 265
See application file for complete search history.

(56) References Cited

U.S. PATENT DOCUMENTS

| | | | |
|---|---|---|---|
| 3,480,136 A | 11/1969 | Poupitch | |
| 4,301,575 A | 11/1981 | Goldberg | |
| 4,607,746 A * | 8/1986 | Stinnette | 206/363 |
| 5,027,478 A | 7/1991 | Suhr | |
| 5,161,909 A | 11/1992 | Crouse et al. | |
| 5,297,889 A | 3/1994 | Crouse et al. | |
| 5,309,604 A | 5/1994 | Poulsen | |
| 5,344,011 A | 9/1994 | DiBernardo et al. | |
| 5,366,444 A | 11/1994 | Martin | |
| 5,419,018 A | 5/1995 | Karlis et al. | |
| 5,511,661 A | 4/1996 | Karlis et al. | |
| 5,702,080 A * | 12/1997 | Whittier et al. | 248/205.5 |
| 5,843,002 A | 12/1998 | Pecor et al. | |
| 6,047,825 A | 4/2000 | Samuels | |
| 6,148,488 A | 11/2000 | Gristock | |
| 6,375,006 B1 | 4/2002 | Samuels | |
| 6,405,414 B1 | 6/2002 | Byrnes et al. | |
| 2003/0060803 A1 | 3/2003 | McGlinch et al. | |
| 2003/0125713 A1 | 7/2003 | McGlinch et al. | |

* cited by examiner

*Primary Examiner*—Luan K Bui
(74) *Attorney, Agent, or Firm*—Crompton, Seager & Tufte, LLC

(57) ABSTRACT

Packaging for an elongated medical device. The packaging may include a packaging structure that is adapted to be self interfacing and/or self mating such that the packaging structure can selectively maintain itself in a coiled, semi-coiled, and/or hoop like configuration without the use of additional structures.

21 Claims, 7 Drawing Sheets

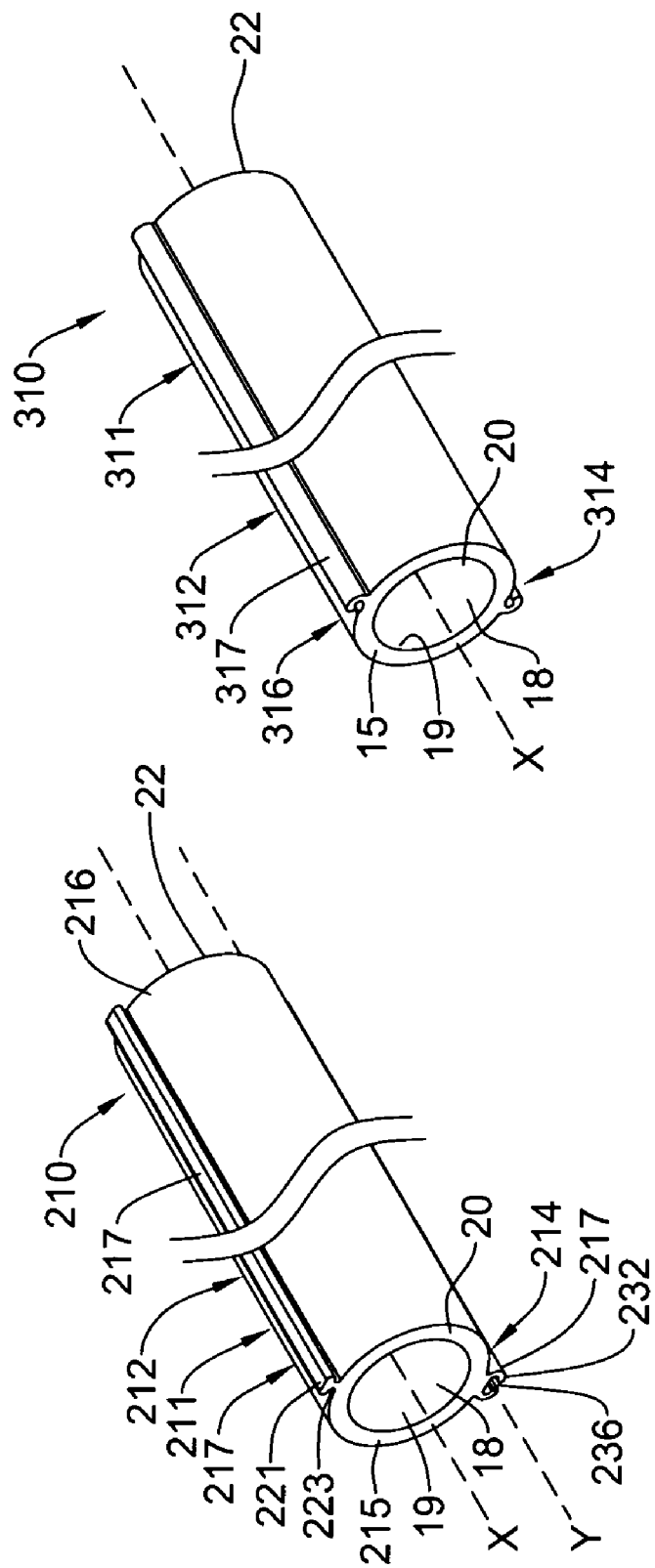

PACKAGING FOR MEDICAL DEVICE

FIELD OF THE INVENTION

The present invention generally relates to packaging for elongated medical devices.

BACKGROUND

Elongate medical devices such as catheters, guide wires, or the like, are often provided or sold in packaging structures and/or assemblies. Packaging structures can provide a convenient way to protect, store, ship, or handle an elongated medical device. A number of different packaging structures and/or assemblies, and methods of making and using packaging structures and/or assemblies are known, each having certain advantages and disadvantages. However, there is an ongoing need to provide alternative structures, assemblies, and methods for making and using structures and/or assemblies for packaging elongated medical devices.

SUMMARY OF EXAMPLE EMBODIMENTS

In some aspects, the invention relates to alternative designs, materials, and methods of making and using structures and/or assemblies for packaging elongate medical devices. Some embodiments include a packaging structure that is adapted to be self-interfacing and/or self-mating such that the packaging structure can selectively maintain itself in a coiled, semi-coiled, and/or hoop like configuration without the use of additional structures. For example, some embodiments include a packaging structure having a first portion comprising an elongated sheath defining a lumen adapted to receive at least a portion of the elongated medical device. The packaging structure may also include a second portion non-releasably attached to and disposed along at least a part of the length of the first portion and extending radially outwardly from the first portion. The second portion defines a connecting structure adapted to engage and mate with a part of the first portion and selectively maintain the packaging structure in a coiled, semi-coiled, or hoop-like configuration.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 7 is a partial perspective view of another example embodiment of a packaging structure for use in packaging an elongated medical device; and FIG. 8 is a partial perspective view of another example embodiment of a packaging structure for use in packaging an elongated medical device.

Figure 1:
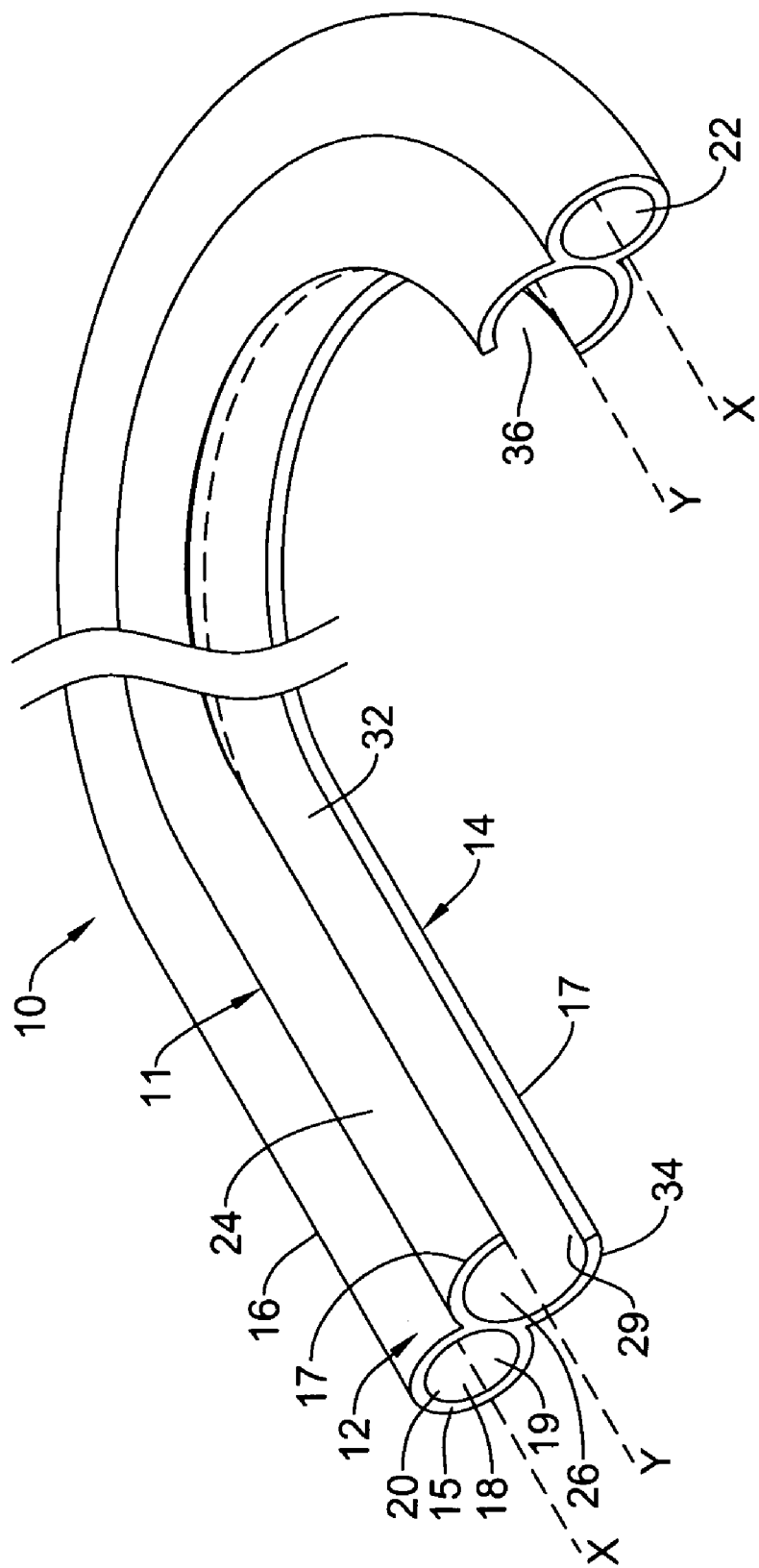
FIG. 1 is a partial perspective view of one example embodiment of a packaging structure for use in packaging an elongated medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS OF THE INVENTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description of some embodiments should be read with reference to the drawings, wherein like reference numerals indicate like elements throughout the several views. The drawings, which are not necessarily to scale, depict some example embodiments and are not intended to limit the scope of the invention. Those skilled in the art and others will recognize that many of the examples provided have suitable alternatives which may also be utilized.

Some embodiments relate to a packaging structure for an elongated medical device that is adapted to be self-interfacing and/or self-mating such that the packaging structure can maintain itself, when so disposed, in a coiled, semi-coiled, and/or hoop-like configuration without the use of additional or separate structures. As will be understood by those of skill in the art and others, it can be desirable to provide packaging for an elongated medical device that can be selectively placed in a coiled, semi-coiled, and/or hoop like configuration. In at least some situations, such configurations are efficient, for example, for storage, transport, and dispensing of elongated medical devices.

Refer now to FIG. 1 which illustrates a partial perspective view of one example embodiment of a packaging structure 10 for use in packaging an elongated medical device. In FIG. 1, the packaging structure 10 is shown in a generally non-coiled configuration. The packaging structure 10 includes a generally elongated body 11 that includes a first portion 12 and a second portion 14. The first and second portions 12/14 of the body 11 are adapted to releasably mate, engage, and/or interface with each other such that the packaging structure 10 can be put into and selectively maintained in the generally coiled, semi-coiled, and/or hoop like configuration. As such, the body 11 is self-interfacing and/or self-mating, in that additional separate structures are not necessary to selectively maintain the structure 10 in a generally coiled, semi-coiled, and/or hoop-like configuration. In general, the first portion 12 is adapted to act as a carrier for an elongated medical device, and the second portion 14 is adapted to mate with and/or interface with at least a part of the first portion 12 to selectively maintain the packaging structure 10 in a coiled, semi-coiled and/or hoop-like configuration.

In the embodiment of FIG. 1, the first portion 12 includes a wall 15 defining an outer surface 16 and a lumen 18 extending along a longitudinal axis x. The lumen 18 may extend along the entire length of the structure 10, or only along a portion thereof. The lumen 18 defines the inner surface 19 of the wall 15, and may have an open proximal end 20 and an-open or closed distal end 22. The lumen 18 can be adapted to accommodate and/or package all or a portion of an elongated medical device therein, as will be discussed in greater detail below. For example, the lumen 18 may be sized or shaped to accommodate the size and shape of the elongated medical device to be packaged.

By way of example, not limitation, the first portion 12 is shown as a generally elongated tubular or sheath-like member having a generally circular cross-sectional shape extending along the longitudinal axis x. As can be appreciated, the lumen 18 has a generally circular cross-sectional shape as well. For example, the first portion 12 may take the general shape and structure of a carrier tube adapted to carry an elongated medical device.

It should be understood, however, that the first portion 12, including the lumen 18 and the outer surface 16, may include and/or define any of a broad variety of shapes and/or structures. For example, in other embodiments, the outer surface 16 and/or the lumen 18 can include a generally oval, square, rectangular, triangular, oblong, or polygonal shape, or the like, or any of a broad variety of other shapes. For example, in some embodiments, the shape of the lumen 18, and to some extent, the outer surface 16, may be dependent upon the particular shape and size of the elongated medical device that is intended to be carried within the structure 10. Additionally, the outer surface 16 may include or define a shape or structure that may be adapted to mate or interface with the second portion 14, as will be discussed in more detail below. A broad variety of such mating or interfacing shapes or structures may be used. The cross-sectional shape of the outer surface 16 and/or the lumen 18 may be generally consistent with or may vary with one another. Furthermore, the cross-sectional shapes of the outer surface 16 and/or of the lumen 18 may be generally constant or may vary along their lengths.

The second portion 14 of the body 11 can be fixedly or non-releasably attached to, or of monolithic or unitary construction with, the first portion 12. The body 11 can be constructed such that the first and second portions 12/14 are maintained in a generally fixed position relative to one another along at least a portion of the length of the structure 10. As such, the body 11 can be considered as one structure including the first and second portions 12/14. As indicated above, the second portion 14 is adapted to mate with and/or interface with at least a part of the first portion 12 to selectively maintain the packaging structure 10 in a desired configuration.

In the embodiment of FIG. 1, the second portion 14 includes one or more walls 17 defining an outer surface 24 and an open lumen or channel 26 extending along a longitudinal axis y. The longitudinal axis y can be generally parallel to longitudinal axis x. The channel 26 may extend along the entire length of the structure 10, or only along a portion or portions thereof. The channel 26 defines the inner surface 29 of the wall 17. An opening 32 is defined in the wall 17 to render the channel 26 open to the exterior. The opening 32 may extend along the length of the second portion 14, and may run generally parallel to the axis y. The channel 26 may have an open or closed proximal end 34 and an open or closed distal end 36. The channel 26 can be adapted to accommodate at least a part of the first portion 14 therein such that when the structure 10 is bent back and/or coiled back upon itself, for example, when placed in a coiled, semi-coiled, and/or hoop-like configuration, the first and second portions 12/14 can releasably engage, mate, and/or interface to selectively maintain the structure 10 in the coiled, semi-coiled, and/or hoop-like configuration.

By way of example, not limitation, the second portion 14 of FIG. 1 is shown as a generally elongated member having a generally semi-circular and/or hemispherical cross-sectional shape extending along the longitudinal axis y. As can be appreciated, the channel 26 has a generally semi-circular and/or hemispherical shape as well. As such, the second portion 14 defines a generally "C-shaped" or "U-shaped" structure extending along the longitudinal axis y that is generally sized and shaped to receive and mate with, and to a certain extent, releasably hold and/or maintain a part of the first portion 12 when the structure 10 is bent back or coiled about itself. The opening 32 in the channel 26 allows for the insertion of part of the first portion 12 into the channel 26 of the second portion 14, and the channel 26 and/or the opening 32 are sized and/or configured to selectively maintain and/or hold part of the first portion 12 therein.

It should be understood, however, that the second portion 14 may include and/or define any of a broad variety of shapes and/or structures that are adapted to mate with the first portion 12. For example, in other embodiments, the channel 26 can include a generally oval, square, rectangular, triangular, oblong, or polygonal shape, or the like, or any of a broad variety of other shapes. It should be also understood that the shape of the second portion 14 can be at least somewhat dependent upon the shape of the first portion 12, such that an appropriate mating engagement and/or interfacing between the two portions can occur to selectively maintain the structure in a desired configuration.

Figure 2:
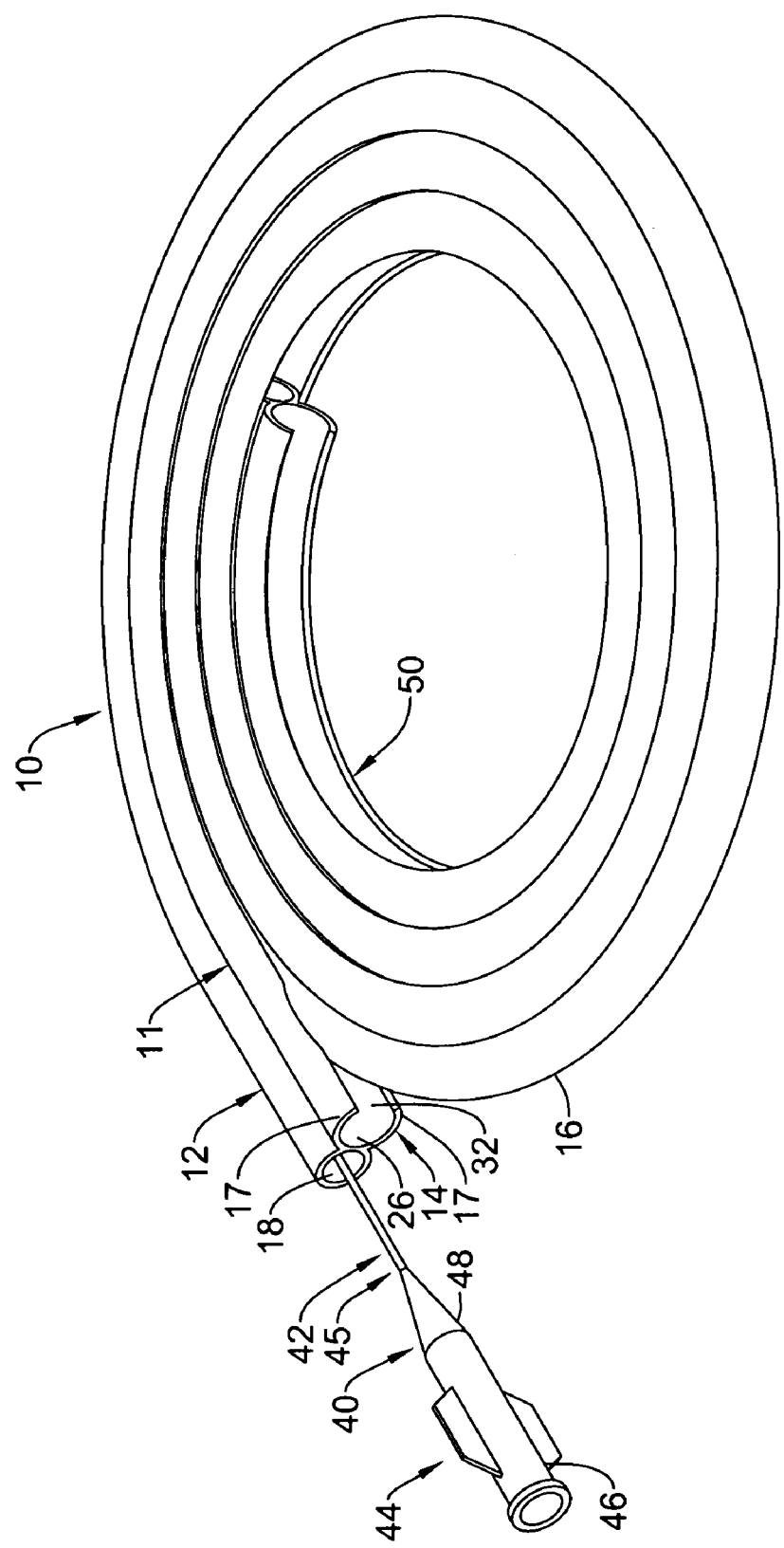
FIG. 2 is a perspective view of the packaging structure of FIG. 1 in a coiled configuration and including an elongated medical device disposed partially therein.
Figure 3:
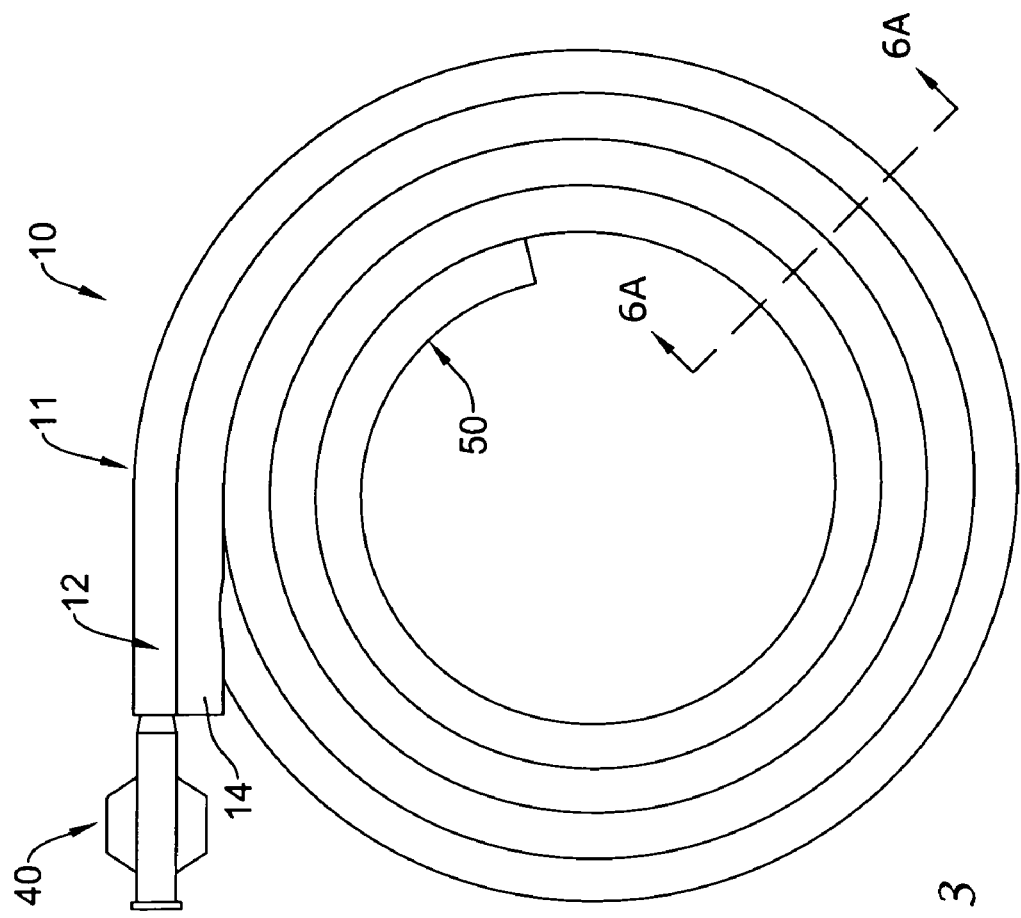
FIG. 3 is a plan view of the packaging structure of FIG. 1 in a coiled configuration and including an elongated medical device disposed therein.

Refer now to FIGS. 2 and 3, which shows the structure 10 in a coiled configuration, wherein the body 11 has been coiled about itself. As the body 11 is coiled about itself, the first portion 12 can be inserted into the channel 26 of the second portion 14 to create a mating engagement. The second portion 14 and/or the first portion 12 may include structure, material, shape, and/or sizing adapted to selectively maintain the first and second portions 12/14 in the mated engagement. For example, it may be desirable that the structure 10 can be selectively maintained in the coiled configuration and resist forces that may cause the structure 10 to become uncoiled, but also may be selectively uncoiled when desired. For example, forces generated by handling, residual stresses in the structure 10 and/or in the medical device packaged therein, gravity, or the like, may act to uncoil the structure 10 at an undesirable time. The structure, material, shape, and/or sizing of the first and second portions 12 may be adapted to overcome these forces, and to selectively maintain and/or hold the first and second portions 12/14 in the mated engagement. For example, in some embodiments, the first and second portions 12/14 can be adapted to create a selectively releasable interference fit or frictional fit with each other.

For example, the opening 32 may be smaller than the outer perimeter and/or circumference of the first portion 12 such that when the first portion 12 is inserted into the channel 26 through the opening 32, the walls 17 first deform to allow the first portion 12 into the channel 26, and thereafter at least partially recover such that they are disposed about a part of the outer surface 16 of the first portion 12 to create an interference and/or frictional fit. The walls 17 of second portion 14 may include a degree of flexibility, elasticity, and/or recoverability allowing for such selective mating engagement and also allowing for the creation of the frictional and/or interference fit to selectively maintain the mating configuration.

Figure 6C:
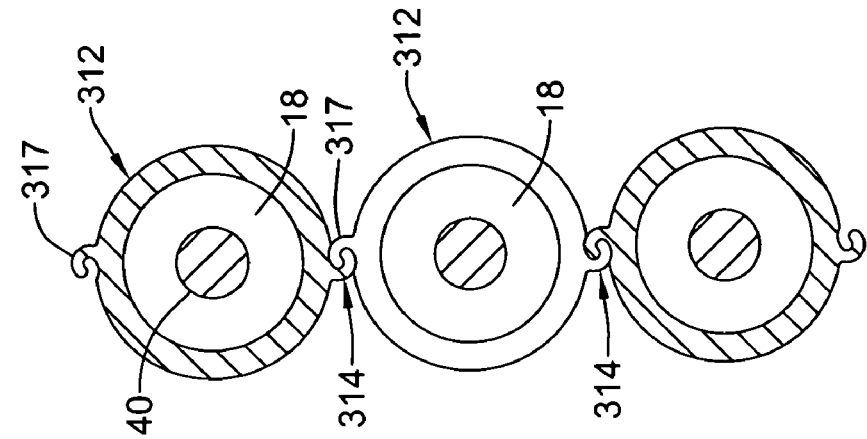
FIG. 6C a cross-sectional view, similar to that of FIG. 6A, of the packaging structure of FIG. 8 when the packaging structure of FIG. 8 is in a coiled configuration.
Figure 6B:
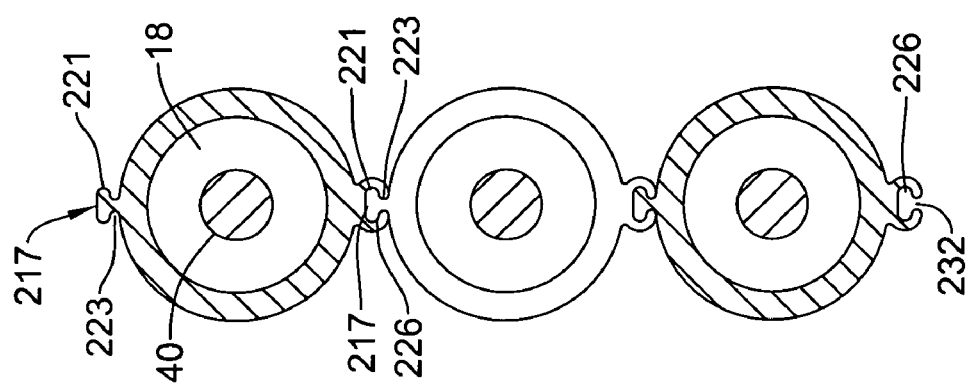
FIG. 6B a cross-sectional view, similar to that of FIG. 6A, of the packaging structure of FIG. 7 when the packaging structure of FIG. 7 is in a coiled configuration.
Figure 6A:
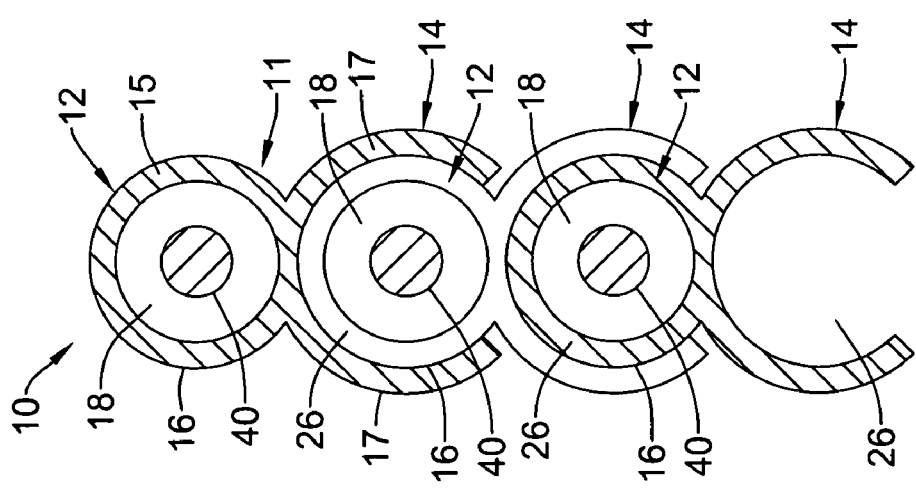
FIG. 6A is a cross-sectional view of the packaging structure of FIG. 3 in taken along line 6A-6A.

For example, refer now to FIG. 6A, which shows a cross-sectional view of the embodiment of FIG. 3, taken along lines 6-6. As can be seen in FIG. 6A, the first portion 12 is disposed within the channel 26 of the second portion 14, and the walls 17 of the second portion extend partially about the outer surface 16 of the first portion to create an interference and/or frictional fit between the two portions 12/14. As such, the mating of the two portions 12/14 provides for frictional and/or interference engagement to selectively maintain the mating configuration.

As can be appreciated, other structures, shapes, sizes, and the like, may be used to create such a selective mating engagement, some of which will be discussed below with reference to other embodiments. For example, the first and second portions 12/14 may include and/or define any of a broad variety of mating shapes, sizes, and/or structures that are adapted to selectively maintain the mated engagement. For example, in other embodiments, the outer surface 16 of the first portion 12 can include or define any of a broad variety of other shapes or structures, and the second portion 14 can include or define shapes or structures that are adapted to selectively mate with the shape and/or structure of the first portion 12.

As can be seen in FIGS. 2 and 3, an elongated medical device 40, such as an intravascular device, is disposed in the lumen 18 of the packaging structure 10 such that the medical device 40 can be carried in and/or packaged by the packaging structure 10. The medical device 40 can be inserted within the packaging structure 10 before, after, and/or during the packaging structure 10 being placed in the coiled, semi-coiled, and/or hoop-like configuration.

Medical device 40 generically refers to a wide variety of elongate medical devices such as catheters, guide wires, or the like. For example, the intravascular device may comprise a balloon catheter, a guide catheter, a diagnostic catheter, a guide wire, a drug delivery catheter, an atherectomy catheter, a tubular sheath, a stent delivery catheter, or the like. For purposes of illustration only, intravascular device 40 is shown in the form of an intravascular catheter 40 having an elongate shaft 42, and a hub assembly 44 connected to the proximal portion 45 of the elongate shaft 42. Hub assembly 44 includes a hub portion 46 and a strain relief 48. The hub 46 and the strain relief 48 may be a two-piece construction or a one-piece construction. The proximal portion 45 of the elongate shaft 42 extends through the strain relief 48 and into the hub 46. The hub assembly 44 may be permanently or releasably connected to the proximal shaft portion 45.

In some embodiments, the packaging structure 10, the hub assembly 44, or other portion of the medical device 40, may be sized and/or may include structure to selectively and releasably connect the medical device 40 to the packaging structure 10. For example, it may be desirable that the medical device 40 can be maintained within the packaging structure 10 and resist gravitational or handling forces which may otherwise cause the device 40 to fall out of the packaging structure 10, but also may be removed from the packaging structure 10 when desired.

For example, in some embodiments, a portion of the medical device 40, such as the hub assembly 44, may include a portion that is sized to create a frictional or interference fit with the inner surface 19 of the lumen 18. In other embodiments, structures, such as an interference fit member (IFM) or other structure may be included on the hub assembly 44, or other portions of the medical device 40 to achieve an interference of frictional fit with the inner surface 19 of the lumen 18, or other portions of the packaging structure 10. Such structure may include one or more protrusions on the hub assembly 44 that are sized and adapted to mate with the inner surface 19 of the lumen 18 to create an interference or frictional fit between the packaging structure 10 and the medical device 40. In some embodiments, parts of the packaging structure 10 and/or the structure on the medical device 40 has sufficient flexibility and/or compressibility to deform and thereby permit the medical device 40 to enter into the lumen 18 despite a nominal difference in size. In yet other embodiments, other structures, such as releasable latches, tapes, adhesives, or the like may be used to assure that the medical device 40 is selectively retained within the lumen 18 until it is desired to remove it. Some example embodiments of structures that may be used to maintain a medical device within a packaging structure include those disclosed in U.S. patent application Ser. Nos. 09/960,260 and 10/244,870, both of which are incorporated herein by reference.

It should be noted that in the embodiment shown in FIGS. 2, 3, and 6A, the second portion 14 extends substantially the entire length of the packaging structure 10. As a result, when the structure 10 is place in a coiled configuration, a segment of the second portion 14, for example segment 50 located adjacent the distal end, does not house any part of the first segment 12. In other arrangements, for example if the structure 10 were coiled in the opposite direction, such an unmated segment of the second portion 14 would be disposed at the proximal end. This is simply due to the inherencies of the coiled configuration—whereby if the second portion 14 extends the entire length of the structure 10, when the structure 10 is in a coiled configuration, at least a segment of the second portion 14 will not be used to house a part of the first portion 12. In some embodiments, for simplicity, the unused segment, for example segment 50, may be left as is. In other embodiments, such unused segments may be trimmed. In yet other embodiments, the unused segment, for example segment 50, may be used to engage or mate with other packaging structures, such as a coiling fixture, a centering ring, other packaging material, or the like.

As discussed above, the packaging structure 10 can be shaped and sized such that an elongated medical device can be packaged within the lumen 18, and such that a portion of the first portion 12 can mate with, and be carried by a portion of the second portion 14. It should be understood that the following particular size and shape configurations are given by way of example only, and a broad variety of other sizes and shapes may be used. In some embodiments, the body 11 of the structure can have an overall length ranging from about 10 to 100 inches. The lumen 18 can have an inside diameter ranging from about 0.10 to 0.30 inches, and the wall 15 may have a thickness ranging from 0.002 to 0.020 inches. The channel 26 can generally define an inside diameter ranging from 0.10 to 0.30 inches, and the walls 17 may have a thickness ranging from 0.002 to 0.020 inches. The opening 32 can have a width of about 0.05 to about 0.25 inches.

The packaging structure 10, including the body 11, may be made utilizing any of a broad variety of materials, dimensions, and techniques. For example, the body 11, or portions thereof, may be formed using extrusion, molding, casting, and/or bonding techniques, or the like. As indicated above, the first and second portions 12/14 are non-releasably attached to each other to form the body 11. For example, the body 11 may be of monolithic, uniform, or integral construction, wherein the first and second portions 12/14 are made of a single continuous piece to form the body 11. In some such embodiments, the body 11, including the first and second portions 12/14, is formed as a single unitary structure through extrusion, molding, and/or casting techniques.

In other embodiments, the first or second portions 12/14, or parts thereof, may be made as separate parts using known techniques, and thereafter permanently or non-releasably attached, affixed, bonded, or otherwise connected to make the body 11. In any case, the first and second portions 12/14 can be attached to each other such that they remain in a fixed relationship with each other along the length of the structure 10.

The body 11 can be made of any of a broad variety of suitable materials, including polymers, metals, metal alloys, composites, and the like. Some example of suitable polymers may include thermoplastics such as fluoropolymers (PTFE, FEP, PFA, CTFE), nylons, phenylene oxides, polyesters, polyethylenes, polypropylene, polyurethanes, or combinations or blends thereof, or the like. Some example of suitable metals or metal alloys may include steel, such as stainless steel, such as 304V, 304L, and 316L stainless steel; aluminum; tin; or the like.

Figure 4:
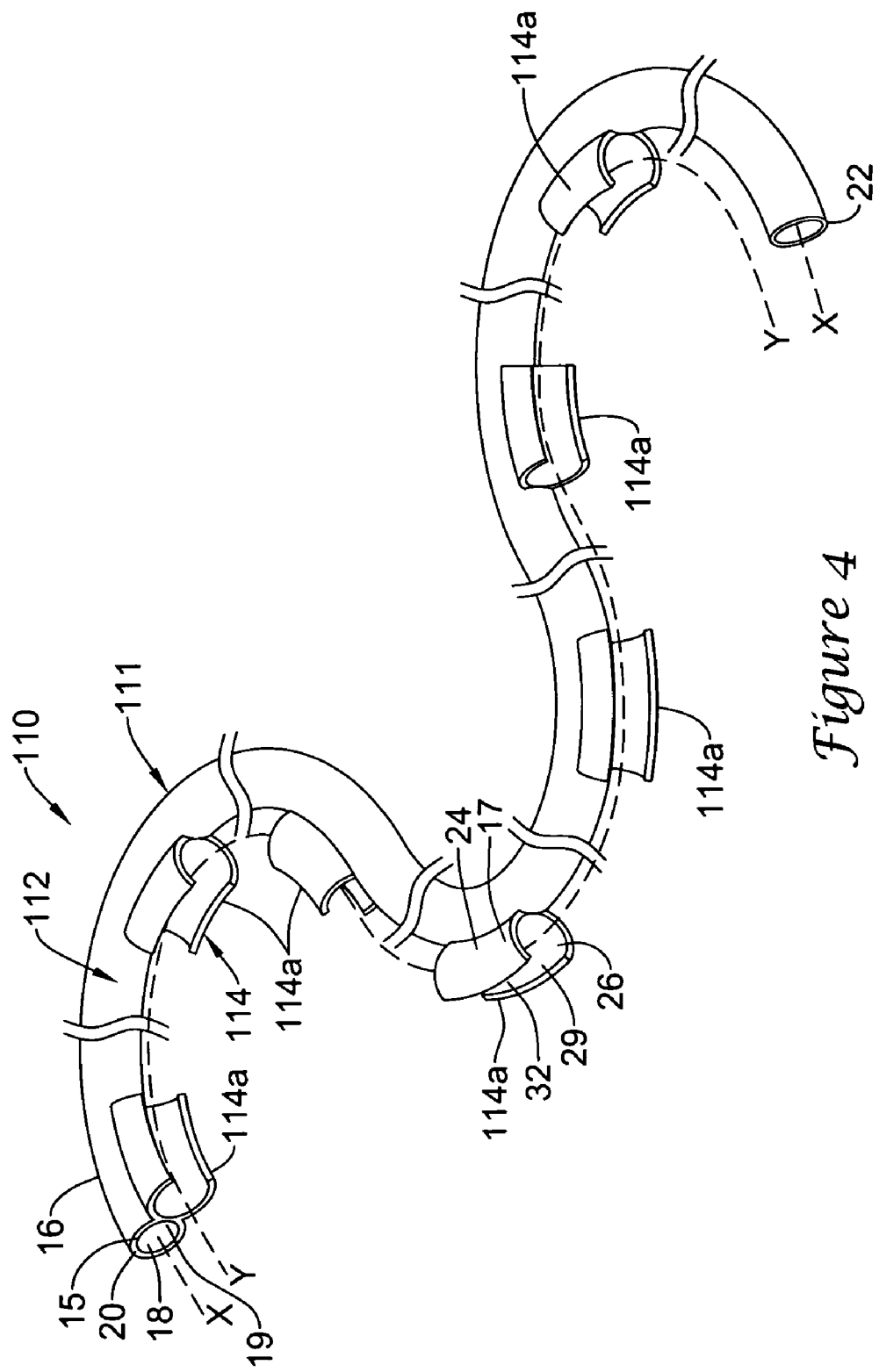
FIG. 4 is a partial perspective view of another example embodiment of a packaging structure for use in packaging an elongated medical device.
Figure 5:
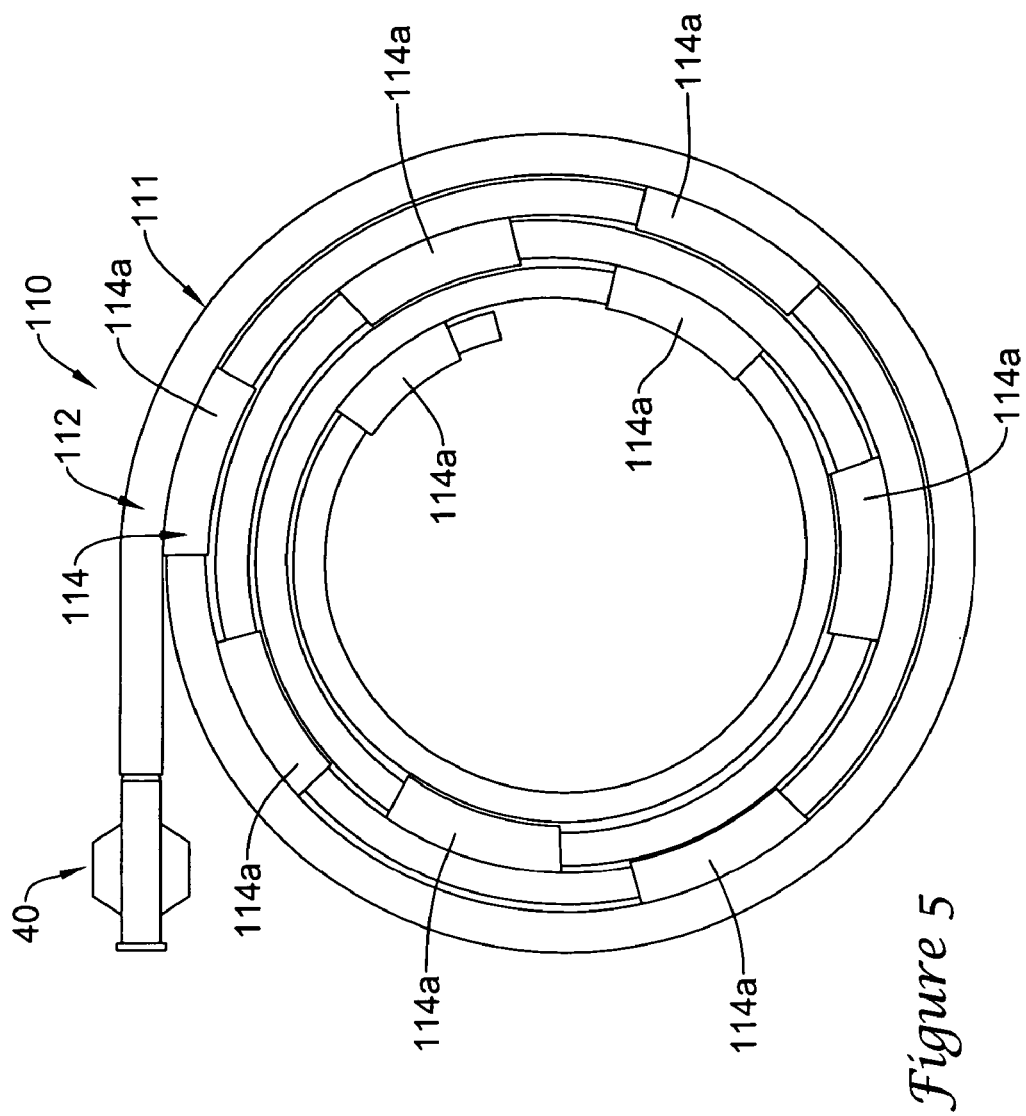
FIG. 5 is a plan view of the packaging structure of FIG. 4 in a coiled configuration and including an elongated medical device disposed therein.

Refer now to FIGS. 4 and 5, which illustrate another embodiment of a packaging structure 110 which is in some respects similar to packaging structure 10, and wherein like reference numbers indicate similar structure. The packaging structure 110 is shown in a generally non-coiled configuration in FIG. 4 and in a coiled configuration with a medical device 40 disposed therein in FIG. 5.

Similar to packaging structure 10, the packaging structure 110 includes a generally elongated body 111 that includes a first portion 112 and a second portion 114. The first portion 112 is generally similar to the first portion 12 discussed above, including a wall 15 defining an outer surface 16 and a lumen 18 extending along a longitudinal axis x. The lumen 18 defines the inner surface 19 of the wall 15, and may have an open proximal end 20 and an open or closed distal end 22. The lumen 18 can be adapted to accommodate and/or package all or a portion of an elongated medical device therein.

In this embodiment, however, the second portion 114 includes a plurality of segments 114a that are separated from each other along the length of the structure 110 along longitudinal axis y. Each of the segments 114a can be similar in structure to the second portion 14 discussed above, but are simply shorter segments that individually do not extend along the entire length of the structure 110. Again, each of the segments 114a can be fixedly and/or non-releasably attached to, or of monolithic or unitary construction with, the first portion 112. The body 111 can be constructed such that segments 114a of the second portion 114 are maintained in a generally fixed position relative to one another, and relative to the first portion 112 along the length of the structure 110. As such, the body 111 can be considered as one structure including the first and second portions 112/114, wherein the second portion 114 is made up of segments 114a. The segments 114a of the second portion 14 are adapted to mate with and/or interface with at least a part of the first portion 112 to selectively maintain the packaging structure 110 in a coiled or semi-coiled configuration.

Similar to the second portion 14, each of the segments 114a of the second portion 114 includes walls 17 defining an outer surface 24 and an open lumen or channel 26 extending along a longitudinal axis y. The channel 26 defined in each segment 114a defines the inner surface 29 of the wall 17. An opening 32 is defined in the walls 17 to render the channel 26 open to the exterior. The channel 26 can be adapted to accommodate at least a part of the first portion 112 therein such that when the structure 110 is bent back and/or coiled back upon itself, for example, when placed in a coiled, semi-coiled, and/or hoop-like configuration, the first and second portions 112/114 can releasably engage, mate, and/or interface to selectively maintain the structure 110 in the coiled, semi-coiled, and/or hoop-like configuration, for example, as shown in FIG. 5.

Additionally, similar to the embodiments discussed above, the second portion 114 and/or the first portion 112 may include structure, material, shape, and/or sizing adapted to selectively maintain the first and second portions 12/14 in the mated engagement. For example, in some embodiments, the first and second portions 112/114 can be adapted to create a selectively releasable interference fit or frictional fit with each other. The structure 110 may be made utilizing any of a broad variety of materials, dimensions, and techniques, including those discussed above.

Refer now to FIG. 7, which illustrates another embodiment of a packaging structure 210 which is in some respects similar to packaging structures 10 and 110 discussed above, wherein like reference numbers indicate similar structure. Similar to packaging structures 10 and 110, the packaging structure 210 includes a generally elongated body 211 that includes a first portion 212 and a second portion 214. The first portion 212 is generally similar to the first portion 12 discussed above, including a wall 215 defining an outer surface 216 and a lumen 18 extending along a longitudinal axis x. The lumen 18 defines the inner surface 19 of the wall 15, and may have an open proximal end 20 and an open or closed distal end 22. The lumen 18 can be adapted to accommodate and/or package all or a portion of an elongated medical device therein.

In this embodiment, however, the outer surface 216 of the first portion 212 defines an elongated protrusion 217 that is adapted to mate with the second portion 214. The elongated protrusion 217 can be fixedly and/or non-releasably attached to, or of monolithic or unitary construction with, the first portion 212. For example, in some embodiments, the protrusion 217 can simply be an extension of the first portion 212, or the outer surface 216, which is created during extrusion, molding, or casting of the structure 210. In other embodiments, the protrusion 217 may be a separate structure that is non-releasably and/or permanently affixed, attached, bonded, or otherwise connected to the first portion 217 during manufacture. The first portion 212 and the protrusion 217 can be constructed such that they are maintained in a generally fixed position relative to one another.

In this embodiment, the protrusion 217 includes a top portion 221 and a base portion 223. The top portion 221 is wider than the base portion 223, and the configuration of the base and top portions are adapted to mate with the second portion 214, as discussed below.

The second portion 214 of the body 211 is similar to the second portion 14 discussed above, but is somewhat smaller, and is adapted to mate with the elongated protrusion 217 of the first portion 214. Again, the second portion 214 is fixedly or non-releasably attached to, or of monolithic or unitary construction with, the first portion 212, and is maintained in a generally fixed position relative to the first portion 212 along at least a portion of the length of the structure 210. As such, the body 211 can be considered as one structure including the first and second portions 212/214.

The second portion 214 includes one or more walls 217 defining an open lumen or channel 226 extending along a longitudinal axis y. The longitudinal axis y can be generally parallel to longitudinal axis x. The channel 226 may extend along the entire length of the structure 210, or only along a portion or portions thereof. An opening 232 is defined in the wall 217 to render the channel 226 open to the exterior. The channel 226 can be adapted to accommodate at least a part of the protrusion 217 of the first portion 214 therein such that when the structure 210 is bent back and/or coiled back upon itself, for example, when placed in a coiled, semi-coiled, and/or hoop-like configuration, the first and second portions 212/214 can releasably engage, mate, and/or interface to selectively maintain the structure 210 in the coiled, semi-coiled, and/or hoop-like configuration.

For example, refer now to FIG. 6B, which shows a cross-sectional view of this embodiment in a mated configuration, and including a medical device 40 disposed within the lumen 18. The top portion 221 of the protrusion 217 can mate with, and be disposed within the channel 226, with the base portion 223 extending through the opening 232. Such an arrangement can be used to create an interference and/or frictional fit to help maintain the structure 210 in the coiled, semi-coiled, and/or hoop-like configuration.

It should also be understood that in other embodiments, the structure of the protrusion 217 and the second portion 214 may vary, but still may be adapted to create the mating engagement. For example, the structure of the protrusion 217 and second portion could be reversed, for example, such that the first portion 212 includes a channel, and the second portion 214 defines a protrusion for mating with the channel. It should also be appreciated by those of skill in the art and others that a broad variety of other shapes and sizes of mating structures may be used, and that these particular structures are given by way of example only.

For example, refer now to FIG. 8, which illustrates another embodiment of a packaging structure 310 which is in some respects similar to packaging structures 10, 110, and 210 discussed above, wherein like reference numbers indicate similar structure. Similar to packaging structures 10, 110, and 210, the packaging structure 310 includes a generally elongated body 311 that includes a first portion 312 and a second portion 314. The first portion 312 is generally similar to the first portion 12 discussed above, in that it includes a wall 15 defining an outer surface 316 and a lumen 18 extending along a longitudinal axis x. The lumen 18 defines the inner surface 19 of the wall 15, and may have an open proximal end 20 and an open or closed distal end 22. The lumen 18 can be adapted to accommodate and/or package all or a portion of an elongated medical device therein.

In this embodiment, however, the outer surface 316 of the first portion 312 defines an elongated protrusion 317 that has a hook-like configuration that is adapted to mate with a hook-like configuration defined by the second portion 314. The hook-like configurations of the elongated protrusion 317 and the second portion 314 can be configured such that they are mirror images of one another, such that when the structure 310 is bent back and/or coiled back upon itself, for example, when placed in a coiled, semi-coiled, and/or hoop-like configuration, the protrusion 317 and the second portion 314 can releasably engage, mate, and/or interface to selectively maintain the structure 310 in the coiled, semi-coiled, and/or hoop-like configuration. For example, refer now to FIG. 6C, which shows a cross-sectional view of this embodiment in a mated configuration, and including a medical device 40 disposed within the lumen 18. The hook-like configuration of the protrusion 317 is shown mated with the hook like second portion 314. Such an arrangement can be used to create an interference and/or frictional fit to help maintain the structure 310 in the coiled, semi-coiled, and/or hoop-like configuration.

Those skilled in the art will recognize that the present invention may be manifested in a variety of forms other than the specific embodiments described and contemplated herein. For example, a broad variety of structures, shapes, and sizes may be used to create the mating interface described herein, and the particular ones shown and described are by way of example only. Accordingly, departures in form and detail may be made without departing from the scope and spirit of the present invention as described in the appended claims.

What is claimed is:

1. A packaging structure for an elongated medical device, the packaging structure comprising:
   a first portion comprising an elongated sheath having a length and defining a lumen having a longitudinal axis extending along at least a portion of the length, the lumen adapted to receive at least a portion of the elongated medical device; and
   a second portion disposed along at least a part of the length of the first portion such that the first portion and the second portion form a monolithic structure, the second portion extending radially outwardly from the first portion relative to the longitudinal axis and including a wall defining a channel, the channel configured to engage and mate with a second part of the first portion and selectively maintain the packaging structure in a coiled, semi-coiled, or hoop-like configuration;
   wherein when the second portion engages the first portion, an inner surface of the second portion is disposed about at least half of a perimeter of an outer surface of the first portion.

2. The packaging structure of claim 1, wherein the channel forms an interference fit with the first portion when mated with the first portion.

3. The packaging structure of claim 2, wherein the interference fit establishes sufficient interference to resist predetermined forces which otherwise would cause the first portion to disengage from the channel.

4. The packaging structure of claim 2, wherein the interference fit establishes interference that is sufficiently small to permit easy disengagement of the first portion from the channel to allow the packaging structure to be taken out of the coiled, semi-coiled, or hoop-like configuration.

5. The packaging structure of claim 1, wherein the channel forms a frictional fit with the first portion when mated with the first portion.

6. The packaging structure of claim 5, wherein the frictional fit establishes sufficient friction to resist predetermined forces which otherwise would cause the first portion to disengage from the channel.

7. The packaging structure of claim 5, wherein the frictional fit establishes friction that is sufficiently small to permit easy disengagement of the first portion from the channel to allow the packaging structure to be taken out of the coiled, semi-coiled, or hoop-like configuration.

8. The packaging structure of claim 1, wherein the first and second portion are defined by an extruded, molded, or cast unitary body.

9. The packaging structure of claim 1, wherein the packaging structure comprises a polymer material.

10. The packaging structure of claim 1, wherein the packaging structure comprises a metal or metal alloy.

11. A packaging structure for an elongated medical device having a length, the packaging structure comprising:
an elongate packaging body having a length, the body including:
an elongated tubular sheath portion defining a lumen extending along at least a portion of the length, the lumen adapted to receive at least a portion of the elongated medical device; and
a generally C-shaped connecting structure portion disposed on a part of the tubular sheath portion, such that the connecting structure portion and the tubular sheath portion form a unitary member, the connecting structure adapted to mate with and releasably attach to a part of the tubular sheath portion
wherein when the connecting structure portion mates with the tubular sheath portion, an inner surface of the connecting structure portion is disposed about at least half of a perimeter of an outer surface of the tubular sheath portion.

12. The packaging structure of claim 11, wherein the connecting structure portion and the tubular sheath portion when mated are adapted to releasably maintain the packaging structure in a coiled, semi-coiled, or hoop-like configuration.

13. The packaging structure of claim 11, wherein the connecting structure portion forms an interference fit with the sheath portion when mated with the sheath portion.

14. The packaging structure of claim 11, wherein the connecting structure portion forms a frictional fit with the sheath portion when mated with the sheath portion.

15. The packaging structure of claim 11, wherein the sheath portion defines an outer surface, and the connecting structure portion defines an elongated channel that is adapted to receive and mate with the outer surface of the sheath portion.

16. The packaging structure of claim 11, wherein the body, including the connecting structure portion and the sheath portion, is defined by a single extruded, molded, or cast unitary structure.

17. The packaging structure of claim 11, wherein the body comprises a polymer material.

18. The packaging structure of claim 11, wherein the body comprises a metal or metal alloy.

19. An assembly comprising:
packaging for an elongated medical device, the packaging including:
a first portion comprising an elongated sheath having a length and defining a lumen having a longitudinal axis extending along at least a portion of the length; and
a second portion disposed along at least a part of the length of the first portion such that the first portion and the second portion form a monolithic structure, the second portion extending radially outwardly from the first portion relative to the longitudinal axis and defining a connecting structure generally corresponding to the shape of the first portion and adapted to mate with and selectively attach to the first portion; and
an elongated medical device at least partially disposed within the lumen;
wherein when the second portion mates with the first portion, an inner surface of the second portion disposed about at least half of a perimeter of an outer surface of the first portion, the packaging structure is maintained in the coiled, semi-coiled, or hoop-like configuration.

20. A method of making packaging structure for an elongated medical device, the method comprising:
creating an elongated packaging body having a length, the body including an elongated tubular sheath portion defining a lumen extending along at least a portion of the length, the lumen adapted to receive at least a portion of the elongated medical device, and a generally C-shaped connecting structure portion disposed on a part of the tubular sheath portion such that the body and the connecting structure form a monolithic structure, the connecting structure adapted to mate with and releasably attach to a part of the tubular sheath portion such that the connecting structure is disposed about at least half of a perimeter of an outer surface of the packaging body.

21. The method of claim 20, wherein the creating includes extruding, molding, or casting the body such that the body is a single unitary structure.

* * * * *